(12) United States Patent
Sun et al.

(10) Patent No.: US 10,712,281 B2
(45) Date of Patent: Jul. 14, 2020

(54) METHOD FOR DETECTING COMPOSITION OF STEEL SAMPLE BY USING MULTI-PULSE LASER-INDUCED PLASMA SPECTROMETER

(71) Applicant: Academy of Opto-Electronics, Chinese Academy of Sciences, Beijing (CN)

(72) Inventors: Hui Sun, Beijing (CN); Zhongwei Fan, Beijing (CN)

(73) Assignee: Academy of Opto-Electronics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/309,556

(22) PCT Filed: Oct. 11, 2016

(86) PCT No.: PCT/CN2016/101742
§ 371 (c)(1),
(2) Date: Dec. 13, 2018

(87) PCT Pub. No.: WO2018/035937
PCT Pub. Date: Mar. 1, 2018

(65) Prior Publication Data
US 2019/0219511 A1    Jul. 18, 2019

(30) Foreign Application Priority Data
Aug. 24, 2016 (CN) .......................... 2016 1 0717184

(51) Int. Cl.
*G01J 3/30* (2006.01)
*G01N 21/71* (2006.01)
(Continued)

(52) U.S. Cl.
CPC .......... *G01N 21/718* (2013.01); *G01N 21/63* (2013.01); *G01N 21/6402* (2013.01); *G01N 33/202* (2019.01); *G01N 2201/06113* (2013.01)

(58) Field of Classification Search
CPC .. G01N 21/63; G01N 21/6402; G01N 21/718; G01N 2201/06113; G01N 33/202
(Continued)

(56) References Cited

U.S. PATENT DOCUMENTS

| 8,310,671 B1 | 11/2012 | Nguyen et al. |
| 2005/0094678 A1* | 5/2005 | Zou ..................... H01S 3/09415 372/12 |

(Continued)

FOREIGN PATENT DOCUMENTS

| CN | 10279801 | * 10/2012 |
| CN | 102709801 A | 10/2012 |

(Continued)

OTHER PUBLICATIONS

International Search Report (PCT/ISA/210) dated May 19, 2017, by the State Intellectual Property Office of the P.R. China Patent Office as the International Searching Authority for International Application No. PCT/CN2016/101742 (English Translation).

*Primary Examiner* — Sunghee Y Gray

(57) ABSTRACT

The present invention relates to a method for detecting steel sample components by using a multi-pulse laser induced plasma spectral analysis device, and in particular, to a method for detecting steel sample components by using a multi-pulse laser induced plasma spectral analysis device that includes picosecond and nanosecond laser pulse widths. A laser induced light source is a laser light source that includes nanosecond and picosecond ultrashort pulses, and one pulse laser device can be used to generate two pulse lasers, namely, a nanosecond and a picosecond laser; the two pulse lasers pass through a same output and focusing light (Continued)

path, so as to ensure that the two pulse lasers are focused on a same position of a sample to be detected; a surface of the sample is irradiated by using a first beam of nanosecond laser pulse to generate plasmas; subsequently, the plasmas are irradiated by using a second beam of picosecond laser pulse to enhance spectral line emission.

8 Claims, 3 Drawing Sheets

(51) Int. Cl.
    *G01N 21/63*     (2006.01)
    *G01N 33/202*     (2019.01)
    *G01N 21/64*     (2006.01)

(58) Field of Classification Search
    USPC .......................................................... 356/318
    See application file for complete search history.

(56) References Cited

U.S. PATENT DOCUMENTS

| | | | |
|---|---|---|---|
| 2012/0099103 A1* | 4/2012 | Hahn | G01N 21/718 356/316 |
| 2012/0253333 A1* | 10/2012 | Garden | A61B 18/203 606/9 |
| 2017/0023484 A1* | 1/2017 | Wang | G01J 3/0213 |
| 2017/0205354 A1* | 7/2017 | Buckley | B07C 5/365 |
| 2017/0234800 A1* | 8/2017 | Zhou | G01N 21/718 356/36 |

FOREIGN PATENT DOCUMENTS

| | | | |
|---|---|---|---|
| CN | 102841075 | * | 12/2012 |
| CN | 102841075 A | | 12/2012 |
| CN | 203385665 U | | 1/2014 |
| CN | 104181146 A | | 12/2014 |
| CN | 105762633 A | | 7/2016 |

* cited by examiner

Nd: YAG Ps Laser

METHOD FOR DETECTING COMPOSITION OF STEEL SAMPLE BY USING MULTI-PULSE LASER-INDUCED PLASMA SPECTROMETER

RELATED APPLICATION

This application is a U.S. National Phase application of International Patent Application No. PCT/CN2016/101742, filed on Oct. 11, 2016; claiming priority to Chinese Patent Application No. 201610717184.2, filed on Aug. 24, 2016. The disclosure of which is herein incorporated by reference in its entirety.

TECHNICAL FIELD

The present invention belongs to the field of detecting components of steel samples, and relates to a method for detecting components of steel sample by using a multi-pulse laser induced plasma spectral analysis device, and in particular, a method for detecting steel sample components by using a multi-pulse laser induced plasma spectral analysis device with picosecond and nanosecond laser pulse widths, and a dual-pulse laser induced plasma spectral analysis device that includes nanosecond and picosecond pulse widths of a laser induced light source and is configured to perform real-time online detection on steel sample components.

BACKGROUND ART

Currently, all dual-pulse LIBS technologies use two laser devices to achieve dual-pulse excitation by means of power supply controlled delay, which increases the cost of the system and needs to focus two paths of lasers respectively, and thus makes it difficult to ensure that the two paths of lasers are focused on the sample to be detected at a same point, and dual-pulse plasma excitation with maximum efficiency cannot be achieved.

Laser Induced Breakdown Spectroscopy (LIBS) is a quantitative analytical technique of emission spectrums generated based on interaction between lasers and materials. This method needs only several micrograms in the measurement process, and therefore can implement non-destructive measurement; element analysis on substances in any physical state can be realized without sample pretreatment, so that the LIBS technology is widely used. The LIBS technology is an optical technology application that can measure and analyze samples as far as tens of meters away, and Its remote analysis capability is very attractive in dangerous, high-temperature or hostile environments. LIBS technology for component analysis lasts only about ten seconds in the entire process, and has good real-time and rapidness. The LIBS technology can be used to quantitatively analyze trace substances by means of calibration, and the limit of detection and accuracy completely satisfy application requirements.

Compared with conventional detection technologies, LIBS technology has unparalleled technical advantages for online in situ detection. However, as a single-pulse LIBS technology has low analytical sensitivity, the application in the trace element detection field is limited. LIBS generates transient plasmas based on interaction between high-power lasers and substances to research emission spectrums of plasmas, so as to achieve qualitative analysis and quantitative analysis on sample components. However, the plasma temperature and density of the single-pulse LIBS excitation are low, and the intensity of the emitted emission spectrum is limited, so the analytical sensitivity is relatively low.

The dual-pulse LIBS technology is to generate plasmas by irradiating a surface of a sample by using a first beam of laser pulse, and subsequently, irradiate the plasmas by using a second beam of laser pulse to enhance spectral line emission, so as to implement two phase distribution optimization of material ablation and plasma excitation and therefore the dual-pulse LIBS technology can effectively improve the signal to noise ratio and the analytical sensitivity. Currently, all the dual-pulse LIBS technologies use two nanosecond lasers to achieve dual-pulse excitation by means of power supply controlled delay, which increases the cost of the system and needs to focus two paths of lasers respectively, and thus makes it difficult to ensure that the two paths of lasers are focused on the sample to be detected at a same point, and dual-pulse plasma excitation with maximum efficiency cannot be achieved.

By exploring results of detection on steel samples by using ultrashort pulse lasers with different pulse widths and analysis of the dual-pulse LIBS technology, we find that two pulse lasers can be generated by using single pulse laser device, wherein the first pulse laser is a nanosecond laser, and the second pulse laser is a picosecond laser; and the two pulse lasers are focused on the sample to be detected at a same position; a surface of the sample is irradiated by using a first beam of nanosecond laser pulse to generate plasmas; and subsequently, the plasmas are irradiated by using a second beam of picosecond laser pulse to enhance spectral line emission, so as to achieve two phases distribution optimization of material ablation and plasma excitation, and therefore the signal to noise ratio can be effectively improved and the analytical sensitivity is promoted. We have developed a dual-pulse laser induced plasma spectral analysis device, with laser pulse widths including two specifications: picosecond and nanosecond.

SUMMARY OF THE INVENTION

Currently, all the dual-pulse LIBS technologies use two nanosecond laser devices to achieve dual-pulse excitation by means of power supply controlled delay, which increases the cost of the system and needs to focus two paths of lasers respectively, and thus makes it difficult to ensure that the two paths of lasers are focused on the sample to be detected at a same point, and dual-pulse plasma excitation with maximum efficiency cannot be achieved.

Because the existing measurement method has the foregoing deficiency, we propose a new dual-pulse laser induced plasma spectral analysis device for measuring steel sample components. The present invention uses an existing all-solid-state regeneration amplifier picosecond laser as a light source of a laser induced plasma spectral analysis device, implements output of a laser induced light source with a picosecond pulse width by using a regeneration amplification technology, and implements output of the laser induced light source with a nanosecond pulse width in a Q-switching manner, so as to achieve a laser induced plasma spectral analysis device with laser pulse widths including two specifications: picosecond and nanosecond. In measurement on steel samples, we find by experiments a dual-pulse laser induced plasma spectral analysis device that includes a first beam of nanosecond laser and a second beam of picosecond laser, which has a better effect than a conventional dual-pulse laser induced plasma spectral analysis device.

Beneficial Effects of the Invention

The benefit of the present invention lies in a dual-pulse laser induced plasma spectral analysis device with laser pulse widths including two specifications: picosecond and nanosecond; two pulse lasers can be generated by using one pulse laser device, wherein the first pulse laser is a nanosecond laser, the second pulse laser is a picosecond laser. With the same output and focusing optical path, the two pulses can be focused on the sample to be measured at a same position. The first nanosecond laser pulse is used to irradiate the surface of the sample to produce plasma, and then the second picosecond laser pulse is used to irradiate the plasma to enhance the emission of spectral lines, so as to achieve the two-stage distribution optimization of material ablation and plasma excitation, and thus the signal-to-noise ratio and the analytical sensitivity can be effectively improved. The reason for this benefit is that all-solid-state regeneration amplifier picosecond laser is used as an inductive light source of a laser induced plasma spectral analysis device, implementing output of the laser induced light source with a picosecond pulse width by using a regeneration amplification technology, and implementing output of the laser induced light source with a nanosecond pulse width in a Q-switching manner, so as to realize a laser induced plasma spectral analysis device with laser pulse widths including two specifications: picosecond and nanosecond. By using the same output and focusing optical path, it is ensured that the two pulsed lasers can be focused on the same position of the sample to be measured. The present application can be applied to a practical detecting device for molten steel composition based on laser-induced plasma spectroscopy for a vacuum induction furnace.

BRIEF DESCRIPTION OF THE DRAWINGS

In FIG. 1:
10: laser induced light source;
20: echelle grating spectrometer;
30: focusing system;
11: laser device;
12: echelle grating spectrometer;
13: integral delay detection system;
14: detection point distance dynamic monitoring system;
15: feedback adjustment control system;
16: light beam quality monitoring and adjusting system;
17: light beam turn-around system; and
18: sample.

In FIG. 2:
1: picosecond laser oscillator, and generates a picosecond laser with a 10-picosecond laser pulse width, a repetition frequency of 90 MHz, and average power of 90 mW;
2: magneto optic isolator;
3: optoelectronic switch; and
4: regeneration amplifier compressor.

DETAILED DESCRIPTION OF THE INVENTION

Figure 1:
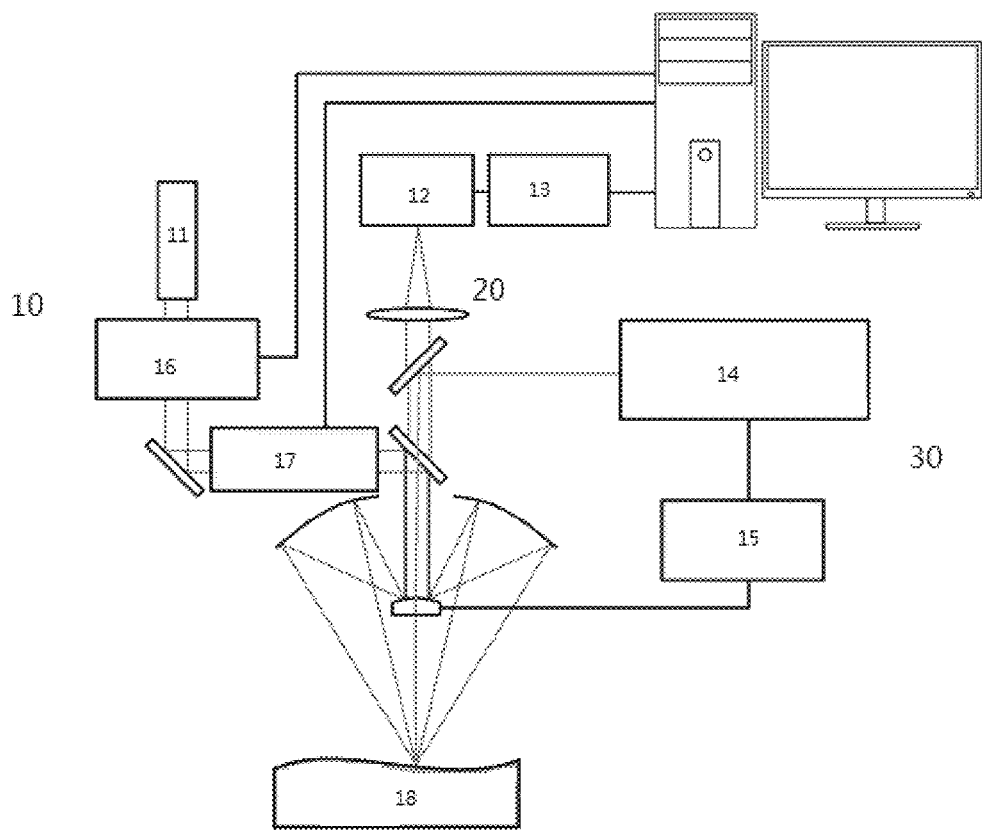
FIG. 1 is a structural diagram of a laser device of the present invention.
Figure 2:
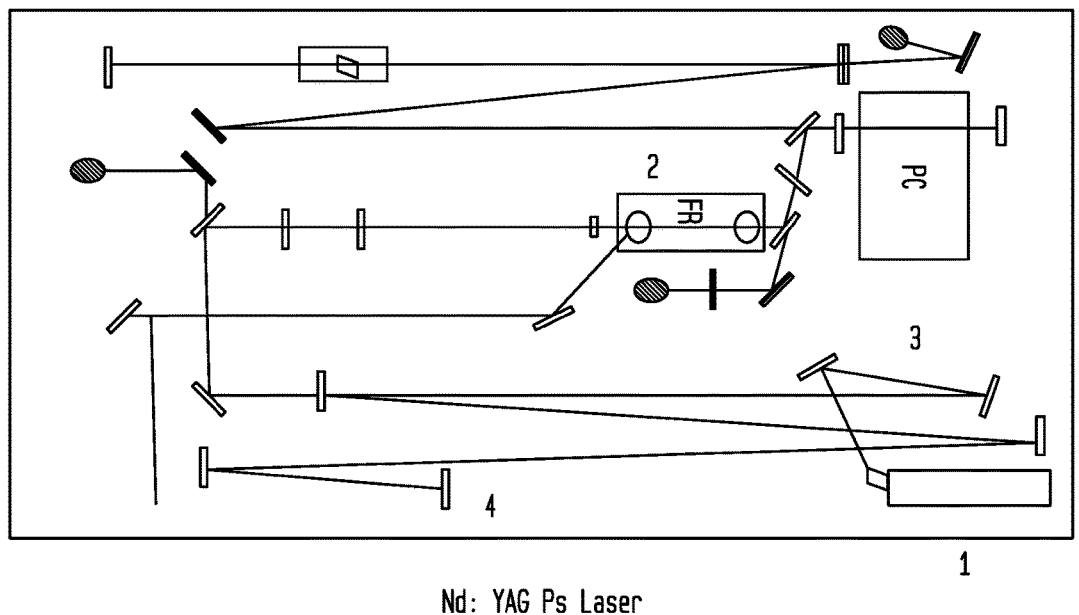
FIG. 2 is a principle diagram of a laser device of the present invention.
Figure 3:
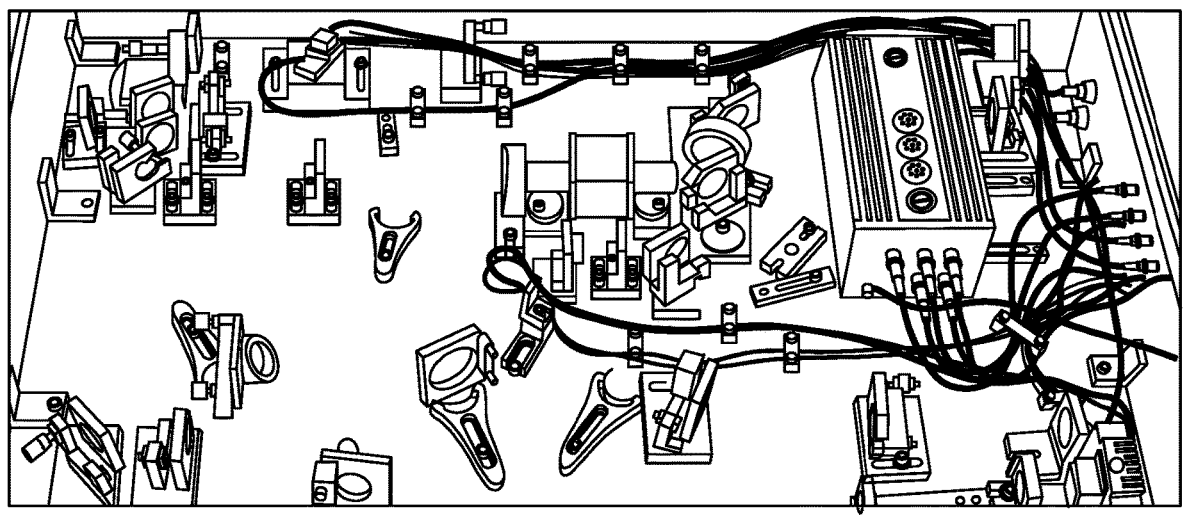
FIG. 3 is a physical diagram of a laser device of the present invention.

A laser import system, a spectrum export and collecting system, a spectroscopic system, and a spectrum receiving system" all are generic terms in the art. The laser import system could be a beam transmission and focusing system that converges the laser light on the surface of the molten steel, for example it may be a few mirrors that transmit light and a telescope that collects light. The spectrum export and collecting system could be the same telescope that gathers light. The spectroscopic system and the spectral receiving system are actually spectrometers (FIGS. 1-2). According to a first embodiment of the present invention, provided is a laser induced plasma spectral analysis device (namely, a multi-pulse laser induced plasma spectral analysis device), wherein the spectral analysis device comprises a laser device, a laser import system, a spectrum export and collecting system, a spectroscopic system, and a spectrum receiving system; the spectrum export and collecting system comprises a spectrum export subsystem and a spectrum collecting subsystem, and the laser device and the spectrum receiving system are controlled by instructions sent by a same pulse generator; the laser device emits laser, which is focused on the sample by means of the laser import system, so that plasmas are formed on the surface of the sample to generate laser induced spectrums, and generated fluorescence is exported to the spectrum collecting subsystem by means of the spectrum export subsystem; and collected spectrums are calculated, processed, and analyzed for qualitative and quantitative testing of the elements contained in the samples. The laser device is an all-solid-state regeneration amplifier picosecond laser, and by means of switching between a regeneration amplification technology and a Q-switching manner, output of the laser induced light source with a picosecond pulse width is realized by using the regeneration amplification technology, and output of the laser induced light source with a nanosecond pulse width is realized in the Q-switching manner; so that laser pulse widths of the laser induced plasma spectral analysis device include two specifications: picosecond and nanosecond (for example, the pulse widths are 8 to 12 nanoseconds and 8 to 12 picoseconds, for example, 10 nanoseconds and 10 picoseconds).

Generally, the regeneration amplification technology means that light beams of a picosecond seed source 1 are injected into a regeneration amplifier by means of a magneto optic isolator 2; laser beams move back and forth in the regeneration amplifier (for example, 60 to 200 times, preferably 80 to 150 times, such as about 100 times); single-pulse energy is gradually amplified to a maximum value, and then emitted out of the regeneration amplifier by means of the magneto optic isolator 2 to implement output of a laser with a picosecond pulse width (that is, output of a laser with a picosecond pulse width is implemented by using the regeneration amplification technology).

Generally, the Q-switching manner means that seed light is blocked by means of a mechanical shutter, and meanwhile, an optoelectronic switch 3 is made to work in a Q-switching mode, and output of a laser with a nanosecond pulse width is implemented in a Q-switching manner.

Preferably, laser focusing of the laser import system is in a focus-adjustable manner, and the spectrum collecting subsystem is constructed as a focus-adjustable system.

According to a second embodiment of the present invention, provided is a method for detecting steel sample components by using the device according to the first implementation manner, wherein the method comprises the following steps:

1) output of the laser induced light source with a nanosecond pulse width is realized by the laser device in a Q-switching manner, so that the output nanosecond laser pulse is focused on the sample by means of the laser import system, and plasmas are formed on the surface of the sample;

2) output of the laser induced light source with a picosecond pulse width is realized by the laser device by means of the regeneration amplification technology, so that the output picosecond laser pulse is also focused on the sample by means of the laser import system, and spectral line emission is enhanced through the plasmas formed by irradiation of the nanosecond laser pulse, to generate laser induced spectrums with enhanced spectral lines;

3) the fluorescence from the generated induced spectrums is exported to the spectrum collecting subsystem by means of the spectrum export subsystem; and 4) the collected spectrums are calculated, processed, and analyzed, so as to perform qualitative and quantitative testing of elements contained in the sample.

Generally, in the foregoing method, the device comprises a laser device, a laser import system, a spectrum export and collecting system, a spectroscopic system, and a spectrum receiving system; the spectrum export and collecting system comprises a spectrum export subsystem and a spectrum collecting subsystem, and the laser and the spectrum receiving system are controlled by instructions sent by a same pulse generator; the laser device emits laser, which is focused on the sample by means of the laser import system, so that plasmas are formed on the surface of the sample to generate laser induced spectrums, and generated fluorescence is exported to the spectrum collecting subsystem by means of the spectrum export subsystem; the collected spectrums are calculated, processed, and analyzed for qualitative and quantitative testing of elements contained in the sample. The laser is an all-solid-state regeneration amplifier picosecond laser, by means of switching between a regeneration amplification technology aid a Q-switching manner, output of the laser induced light source with a picosecond pulse width is realized by the regeneration amplification technology, and output of the laser induced light source with a nanosecond pulse width is realized in the Q-switching manner.

According to a third embodiment of the present invention, provided is a method for detecting steel sample components by using a laser induced plasma spectral analysis device, wherein the spectral analysis device comprises a laser device, a laser import system, a spectrum export and collecting system, a spectroscopic system, and a spectrum receiving system; the spectrum export and collecting system comprises a spectrum export subsystem and a spectrum collecting subsystem, and the laser and the spectrum receiving system are controlled by instructions sent by a same pulse generator; the laser device emits laser, which is focused on the sample by means of the laser import system, so that plasmas are formed on the surface of the sample to generate laser induced spectrums, and generated fluorescence is exported to the spectrum collecting subsystem by means of the spectrum export subsystem; the collected spectrums are calculated, processed, and analyzed for qualitative and quantitative testing of elements contained in the sample. The laser is an all-solid-state regeneration amplifier picosecond laser, by means of switching between a regeneration amplification technology and a Q-switching manner, output of the laser induced light source with a picosecond pulse width is realized by using the regeneration amplification technology, and output of the laser induced light source with a nanosecond pulse width is realized in the Q-switching manner; the method comprises the following steps:

1) output of the laser induced light source with a nanosecond pulse width is realized by the laser device in a Q-switching manner, so that the output nanosecond laser pulse is focused on the sample by means of the laser import system, and plasmas are formed on the surface of the sample;

2) output of the laser induced light source with a picosecond pulse width is realized by the laser device by means of the regeneration amplification technology, so that the output picosecond laser pulse is also focused on the sample by means of the laser import system, and spectral line emission is enhanced through the plasmas formed by irradiation of the nanosecond laser pulse, to generate laser induced spectrums with enhanced spectral lines:

3) the fluorescence from the generated induced spectrums is exported to the spectrum collecting subsystem by means of the spectrum export subsystem; and 4) the collected spectrums are calculated, processed, and analyzed, so as to perform qualitative and quantitative testing of elements contained in the sample.

In the present application, preferably, the regeneration amplification technology means that light beams of a picosecond seed source are injected into a regeneration amplifier by means of a magneto optic isolator; laser beams move back and forth in the regeneration amplifier (for example, 60 to 200 times, such as about 100 times); single-pulse energy is gradually amplified to a maximum value, and then emitted out of the regeneration amplifier by means of the magneto optic isolator to implement output of a laser with a picosecond pulse width (that is, output of a laser with a picosecond pulse width is implemented by using the regeneration amplification technology).

Generally, the Q-switching manner means that seed light is blocked by means of a mechanical shutter, and meanwhile, an optoelectronic switch is made to work in a Q-switching mode, and output of a laser with a nanosecond pulse width is implemented in a Q-switching manner.

Preferably, laser focusing of the laser import system is in a focus-adjustable manner, and the spectrum collecting subsystem is configured as a focus-adjustable system.

Preferably, the output nanosecond laser pulse and the output picosecond laser pulse pass through a same output and focusing light path, so as to ensure that the two pulse lasers are focused on a same position of a sample to be detected.

Preferably, the laser device implements switching between the regeneration amplification technology and the Q-switching manner by using an electronic control system including: a main control unit, an LD driving unit, a temperature control unit, a radio frequency control unit, and an outer space unit (referring to external control, generally a computer).

Preferably, the all-solid-state regeneration amplifier picosecond laser has the following working manner: light beams of the seed source are injected into the regeneration amplifier by means of the magneto-optic isolator; laser beams move back and forth in the regeneration amplifier; single-pulse energy is gradually amplified to a maximum value, and then emitted out of the regeneration amplifier by means of the magneto-optic isolator to achieve output of a laser with a picosecond pulse width by using regeneration amplification technology. Furthermore, seed light is blocked by means of the mechanical shutter, and meanwhile, an electro-optical switch is made to work in a Q-switching mode, output of the laser with the nanosecond pulse width is realized by the Q-switching mode, thereby generating laser pulse widths with two specifications, i.e., picosecond and nanosecond laser pulse widths.

Generally, the electronic control unit of the laser comprises external trigger control circuit protection, and temperature early warning functions.

More specifically, a laser induced plasma spectral analysis device mainly comprises six parts: a laser device, a laser import system, a spectrum export and collecting system, a spectroscopic system, and a spectrum receiving system, wherein the laser device and the spectrum receiving system are controlled by instructions sent by a same pulse generator. The laser device transmits laser, which is focused on the sample by means of the laser import system, so that plasmas are formed on the surface of the sample to generate laser induced spectrums, and generated fluorescence is exported to the spectrum collecting subsystem by means of the export system; the collected spectrums are calculated, processed, and analyzed for qualitative and quantitative testing of elements contained in the sample. The developed LIPS mainly comprises a pulse laser device, a laser focusing and signal light collecting systems, a spectrometer system, and a computer system. The laser focusing and signal light collecting systems are designed as focus-adjustable systems to implement accurate measurement; meanwhile, computer software needs to be developed to implement rapid analysis on LIPS spectrums, thereby obtaining real-time component information of the measured steel. The overall schematic diagram of the system is as shown in FIG. 1.

The inventor of the present application develops a set of all-solid-state regeneration amplifier picosecond laser device. A picosecond seed source is a commercial product, and comes from HIGH Q Company of Austrian, and generates a picosecond laser with a 10-picosecond laser pulse width, a repetition frequency of 90 MHz, and average power of 90 mW. Light beams of the seed source are injected into the regeneration amplifier by means of the magneto-optic isolator. Laser beams move back and forth in the regeneration amplifier (for example, 60 to 200 times, preferably 80 to 150 times, such as about 100 times); single-pulse energy is gradually amplified to a maximum value, and then emitted out of the regeneration amplifier by means of the magneto-optic isolator. Output of a laser with a picosecond pulse width is implemented by using a regeneration amplification technology. Seed light can also be blocked by means of a mechanical shutter, and meanwhile, an optoelectronic switch is made to work in a Q-switching mode, and output of a laser with a nanosecond pulse width is implemented in a Q-switching manner, so as to achieve a laser induced plasma spectral analysis device with laser pulse widths including two specifications: picosecond and nanosecond.

The electronic control unit has functions such as external trigger control, circuit protection, and temperature early warning. The electronic control unit mainly comprises: a main control unit, an LD driving unit, a temperature control unit, a radio frequency control unit, an outer space unit (referring to external control, generally a computer) and the like, and further comprises: a laser pump power supply and a control system which needs the functions of displaying working current and voltages, attaching a protection lock and the like; Q switch power supply, which is configured to control output pulse widths and perform pulse laser output control and meanwhile can implement control on output laser modes, to ensure output of a laser induced light source with a picosecond pulse width by using a regeneration amplification technology, and output of a laser induced light source with a nanosecond pulse width in a Q-switching manner. The electronic control system has advantages such as high integrity, simple operation, reliable performance, and at the same time, has functions such as over-current, over-voltage, and overheating protection.

The present invention uses an all-solid-state regeneration amplifier picosecond laser device as an inductive light source of a laser induced plasma spectral analysis device, output of the laser induced light source with a picosecond pulse width is achieved by using regeneration amplification technology, and output of the laser induced light source with a nanosecond pulse width is achieved by Q-switching mode, thereby obtaining a laser induced light source with laser pulse widths including two specifications: picosecond and nanosecond. Two pulse lasers can be generated by using one pulse laser device, wherein the first pulse laser is a nanosecond laser, and the second pulse laser is a picosecond laser. With the same output and focusing optical path, the two pulses can be focused on the sample to be measured at a same position. The first nanosecond laser pulse is used to irradiate the surface of the sample to produce plasma, and then the second picosecond laser pulse is used to irradiate the plasma to enhance the emission of spectral lines, so as to achieve the two-stage distribution optimization of material ablation and plasma excitation, and thus the signal-to-noise ratio and the analytical sensitivity can be effectively improved.

Figure 5:
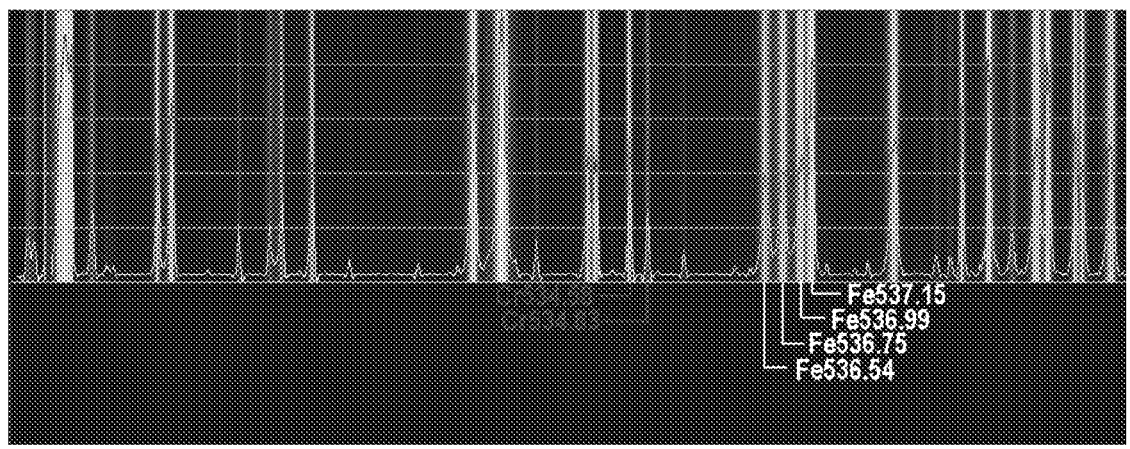
FIG. 5 is a spectrum obtained through ablating steel samples by means of single-pulse femtosecond lasers generated from the method described in the present invention and inducing plasmas by means of lasers.

The present application provides a new laser induced plasma spectral analysis device for measuring steel sample components. The characteristic thereof is that the laser induced light source does not generate common pulse lasers with pulse widths of 10 to 20 nanoseconds, instead, a laser light source that includes nanosecond (for example, 10 nanoseconds) and picosecond (for example, 10 picoseconds) ultra-short pulses. Two pulse lasers can be generated by using one pulse laser device, wherein the first pulse laser is a nanosecond laser, and the second pulse laser is a picosecond laser. The two pulse lasers pass through the same output and focusing light path, so as to ensure that the two pulse lasers are focused on the same position of a sample to be detected. A surface of the sample is irradiated by using a first beam of nanosecond laser pulse to generate plasmas; and subsequently, the plasmas are irradiated by using a second beam of picosecond laser pulse to enhance spectral line emission, thereby achieving distribution optimization of two phases: material ablation and plasma excitation, and therefore the signal to noise ratio can be effectively improved and the analytical sensitivity is increased. FIG. 5 shows a result of a spectrum obtained by ablating steel samples by using single-pulse femtosecond lasers generated by the method described in the present invention and inducing plasmas by using lasers.

Figure 4:
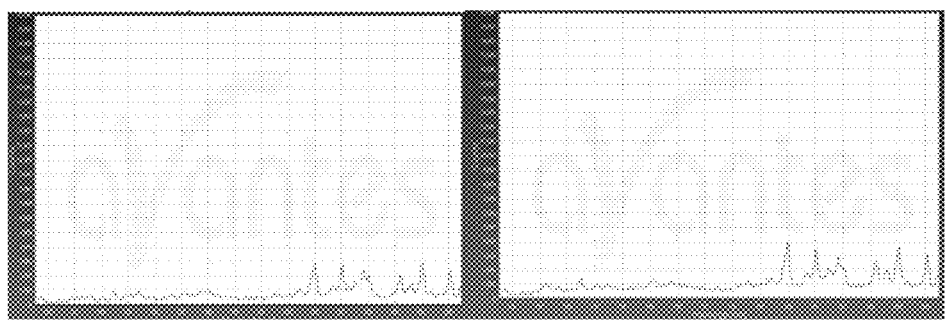
FIG. 4 is a spectrum obtained through ablating steel samples by means of single-pulse lasers generated from the method described in the present invention and inducing plasmas by means of lasers.

We construct experimental apparatuses to perform experimental verification according to the present invention, and the result of the experimental verification is as shown in FIG. 1. We propose a new laser induced plasma spectral analysis device for measuring steel sample components. The characteristic thereof is that the laser induced light source does not generate common single-pulse lasers with pulse widths of 10 to 20 nanoseconds, instead, a laser light source that includes 10 nanoseconds and 10 picoseconds ultra-short pulses. Two pulse lasers can be generated by using one pulse laser device, wherein the first pulse laser is a nanosecond laser; the second pulse laser is a picosecond laser, and the two pulse lasers are focused on the sample to be detected at a same position; a surface of the sample is irradiated by using a first beam of nanosecond laser pulse to generate plasmas; and subsequently, the plasmas are irradiated by using a second beam of picosecond laser pulse to enhance spectral line emission, thereby achieving distribution optimization of two phases: material ablation and plasma excitation, and therefore the signal to noise ratio can be effectively improved and the analytical sensitivity is increased. FIG. 4 is a spectrum obtained by ablating steel samples by using single-pulse lasers generated from the method described in the present invention and inducing plasmas by using lasers. Comparison between spectrums that respectively have a single-pulse-width 10-nanosecond laser induced light source and two pulse widths of 10 nanoseconds and 10 picoseconds can be seen, and the spectrum line enhancement effect is obvious, and therefore is more advantageous to measurement.

The invention claimed is:

1. A method for detecting steel sample components by using a laser induced plasma spectral analysis device, wherein the spectral analysis device comprises a laser device, wherein the laser device is an all-solid-state regeneration amplifier picosecond laser; and by means of switching between a regeneration amplification technology and a Q-switching manner, output of the laser induced light source with a picosecond pulse width is realized by using the regeneration amplification technology, and output of the laser induced light source with a nanosecond pulse width is realized in the Q-switching manner, a laser import system, a spectrum export and collecting system, a spectroscopic system, and a spectrum receiving system; wherein the spectrum export and collecting system comprises a spectrum export subsystem and a spectrum collecting subsystem, the laser and the spectrum receiving system are controlled by instructions sent by a same pulse generator; the laser device transmits laser, which is focused on the sample by means of the laser import system, so that plasmas are formed on the surface of the sample to generate laser induced spectrums, and generated fluorescence is exported to the spectrum collecting subsystem by means of the spectrum export subsystem; the collected spectrums are calculated, processed, and analyzed, so as to perform qualitative and quantitative testing of elements contained in the sample; the method comprises the following steps:

1) output of the laser induced light source with a nanosecond pulse width, so that the output nanosecond laser pulse is focused on the sample by means of the laser import system, and plasmas are formed on the surface of the sample;

2) output of the laser induced light source with a picosecond pulse width, so that the output picosecond laser pulse is also focused on the sample by means of the laser import system, and spectral line emission is enhanced through the plasmas formed by irradiation of the nanosecond laser pulse, to generate laser induced spectrums with enhanced spectral lines;

3) the fluorescence from the generated induced spectrums is exported to the spectrum collecting subsystem by means of the spectrum export subsystem; and 4) the collected spectrums are calculated, processed, and analyzed, so as to perform qualitative and quantitative testing of elements contained in the sample.

2. The method according to claim 1, wherein the regeneration amplification technology comprises that light beams of a picosecond seed source are injected into a regeneration amplifier by means of a magneto-optic isolator; laser beams move back and forth in the regeneration amplifier; single-pulse energy is gradually amplified to a maximum value, and then emitted out of the regeneration amplifier by means of the magneto-optic isolator to implement output of a laser with a picosecond pulse width.

3. The method according to claim 1, wherein the Q-switching manner comprises that seed light is blocked by means of a mechanical shutter, and meanwhile, an optoelectronic switch is made to work in a Q-switching mode, and output of a laser with a nanosecond pulse width is implemented in a Q-switching manner.

4. The method according to claim 1, wherein laser focusing of the laser import system is focused in a focus-adjustable manner, and the spectrum collecting subsystem is configured as a focus-adjustable system.

5. The method according to claim 1, wherein the output nanosecond laser pulse and the output picosecond laser pulse pass through a same output light path and a same focusing light path, so as to ensure that the two pulse lasers are focused on a same position of the sample to be detected.

6. The method according to claim 1, wherein the laser realizes switching between the regeneration amplification technology and the Q-switching manner by using an electronic control system including: a main control unit, an LD driving unit, a temperature control unit, a radio frequency control unit, and an outer space unit.

7. The method according to claim 6, wherein the electronic control unit of the laser has external trigger control, circuit protection, and temperature early warning functions.

8. The method according to claim 1, wherein an all-solid-state regeneration amplifier picosecond laser has following working manner: light beams of the seed source are injected into the regeneration amplifier by means of the magneto-optic isolator; laser beams move back and forth in the regeneration amplifier; single-pulse energy is gradually amplified to a maximum value, and then emitted out of the regeneration amplifier by means of the magneto optic isolator to achieve output of a laser with a picosecond pulse width by using regeneration amplification technology; and furthermore, seed light is blocked by means of the mechanical shutter, and meanwhile an optoelectronic switch is made to work in a Q-switching mode, output of the laser with the nanosecond pulse width is realized by the Q-switching mode, thereby generating laser pulse widths with two specifications: picosecond and nanosecond laser pulse widths.

\* \* \* \* \*